United States Patent
Tacktill

(10) Patent No.: US 10,478,236 B2
(45) Date of Patent: Nov. 19, 2019

(54) METAL ALLOY MONO AND POLY-FILAMENT WIRE REINFORCED CARBON FIBER PLATING SYSTEM

(71) Applicant: Elemental Orthopedics LLC, North Miami, FL (US)

(72) Inventor: Jordan Tacktill, Delray Beach, FL (US)

(73) Assignee: Elemental Orthopedics LLC, North Miami, FL (US)

( * ) Notice: Subject to any disclaimer, the term of this patent is extended or adjusted under 35 U.S.C. 154(b) by 456 days.

(21) Appl. No.: 14/759,049

(22) PCT Filed: Jan. 3, 2014

(86) PCT No.: PCT/US2014/010218
§ 371 (c)(1),
(2) Date: Jul. 2, 2015

(87) PCT Pub. No.: WO2014/107601
PCT Pub. Date: Jul. 10, 2014

(65) Prior Publication Data
US 2015/0335364 A1    Nov. 26, 2015

Related U.S. Application Data

(60) Provisional application No. 61/749,086, filed on Jan. 4, 2013.

(51) Int. Cl.
*A61B 17/80* (2006.01)
*B32B 37/18* (2006.01)
(Continued)

(52) U.S. Cl.
CPC .......... *A61B 17/8047* (2013.01); *A61B 17/72* (2013.01); *A61B 17/80* (2013.01);
(Continued)

(58) Field of Classification Search
CPC ................................. A61B 17/8047
See application file for complete search history.

(56) References Cited

U.S. PATENT DOCUMENTS

2002/0123750 A1 * 9/2002 Eisermann ............. A61B 17/68
606/285
2006/0079900 A1    4/2006 Mathieu et al.
(Continued)

FOREIGN PATENT DOCUMENTS

EP      0551574 A1    7/1993
WO    2014107601 A1   7/2014

OTHER PUBLICATIONS

International Search Report of related PCT/US2014/010218, dated May 1, 2014, 14 pages.
(Continued)

*Primary Examiner* — Olivia C Chang
(74) *Attorney, Agent, or Firm* — Casimir Jones, S.C.; David Casimir

(57) ABSTRACT

The invention entails metal alloy mono and poly-filament wire reinforced carbon fiber plating system for the fixation of skeletal fractures and osteotomies. Current fracture fixation plating systems are metal alloy designs that block the field of vision of the fracture during radiographic evaluation. Carbon fiber and mono and poly-filament wire plating systems reduce the weight and thickness as compared to the current plating designs while permitting direct visualization of the fracture site during the healing process. The benefits of the plating design contribute to the satisfaction of the patient and reduce disruption to the surrounding soft tissue structures. An embodiment of the plating system entails layered sheets of carbon fiber with an infrastructural framework of metal alloy mono and poly-filament wire for added strength and durability of the plate. This system can be utilized for all types of skeletal fracture and osteotomy fixation as well as fields of mechanical, aerospace, and structural engineering where durable lightweight, high strength materials are required.

19 Claims, 7 Drawing Sheets

(51) Int. Cl.
  *B32B 37/10* (2006.01)
  *A61L 31/02* (2006.01)
  *A61L 31/12* (2006.01)
  *A61L 31/14* (2006.01)
  *A61B 17/72* (2006.01)

(52) U.S. Cl.
  CPC ...... *A61B 17/8061* (2013.01); *A61B 17/8066* (2013.01); *A61B 17/8071* (2013.01); *A61B 17/8076* (2013.01); *A61L 31/022* (2013.01); *A61L 31/024* (2013.01); *A61L 31/124* (2013.01); *A61L 31/14* (2013.01); *B32B 37/10* (2013.01); *B32B 37/18* (2013.01); *A61L 2430/02* (2013.01); *B32B 2535/00* (2013.01)

(56) References Cited

U.S. PATENT DOCUMENTS

| | | | |
|---|---|---|---|
| 2010/0016858 A1 | 1/2010 | Michel | |
| 2011/0218570 A1* | 9/2011 | Felix | A61B 17/7059 606/246 |
| 2011/0282395 A1 | 11/2011 | Beyar et al. | |
| 2013/0079829 A1* | 3/2013 | Globerman | A61B 17/1728 606/286 |
| 2013/0289628 A1* | 10/2013 | Fritzinger | A61B 17/8047 606/290 |
| 2015/0257799 A1* | 9/2015 | Janna | A61F 5/05 606/328 |
| 2015/0335364 A1 | 11/2015 | Tacktill | |
| 2017/0000536 A1 | 1/2017 | Tacktill | |

OTHER PUBLICATIONS

Ali et al., "Carbon fibre composite bone plates. Development, evaluation and early clinical experience." J Bone Joint Surg Br. Jul. 1990;72(4):586-91.

Arthrex paget, http://www.arthrex.com/foot-ankle/ankle-fracture-plates, retrieved on: Apr. 28, 2017, 3 pages.

Barber (1991). Prehistoric Textiles. Princeton University Press. Table of Contents provided.

Figure 14:
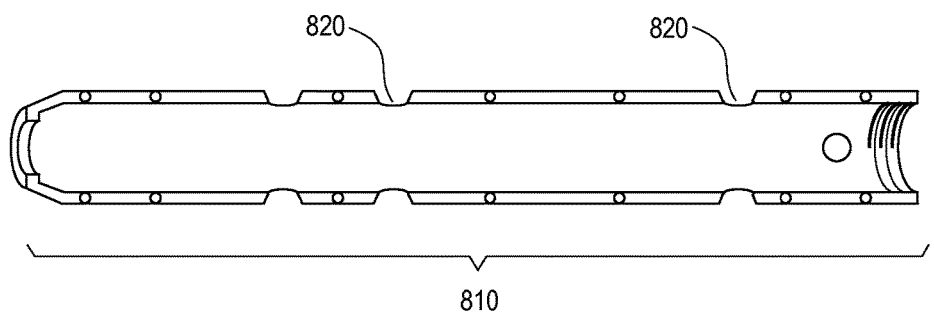

Boeing page, http://www.boeing.com/commercial/aeromagazine/aero_07/corrosn.html#fig14, retrieved on: Apr. 28, 2017, 9 pages.

Burnham (1980). Warp and Weft: A Textile Terminology. Royal Ontario Museum. Table of Contents provided.

Campbell, Elements of Metallury and Engineering Alloys, p. 328, 2008.

Easy Composites page, http://www.easycomposites.co.uk/Learning/Carbon-Fibre-Cloth-Explained.aspx, retrieved on Apr. 28, 2017. 2 pages.

Element 6 page, http://element6composites.com/technical-cf.asp, retrieved on: Apr. 28, 2017, 3 pages.

Epoxy Wikipedia page, http://en.wikipedia.org/wiki/Epoxy, retrieved on: Apr. 28, 2017, 11 pages.

Frost, "The biology of fracture healing. An overview for clinicians. Part I." Clin Orthop Relat Res. Nov. 1989; (248):283-93.

Orthofracs page, http://www.orthofracs.com/adult/trauma/principles/fracture-classification/internal-fixation.html, retrieved on: Apr. 28, 2017, 3 pages.

Princeton Edu page, http://www.princeton.edu/~achaney/tmve/wiki100k/docs/Metal_matrix_composite, retrieved on: Apr. 28, 2017, 4 pages.

Szczêsny et al., "Bacteriology of callus of closed fractures of tibia and femur." J Trauma. Oct. 2008;65(4):837-42.

Tavakkolizadeh et al., "Galvanic Corrosion of Carbon and Steel in Aggressive Environments" Journal of Composites for Construction, 2001, p. 200-210.

Tayton, "Corrosive effect of carbon-fibre reinforced plastic on stainless-steel screws during implantation into man." J Med Eng Technol. Jan.-Feb. 1983;7(1):24-6.

Xiong et al., "Shear and bending performance of carbon fiber composite sandwich panels with pyramidal truss cores." Acta Materialia 60 (2012) 1455-1466.

Archive org page, http://www.benecorinc.com/titanium.php, captured Aug. 2013, retrieved Jul. 3, 2017, 1 page.

* cited by examiner

METAL ALLOY MONO AND POLY-FILAMENT WIRE REINFORCED CARBON FIBER PLATING SYSTEM

The present application is a 371 U.S. National Phase Entry of pending International Application No. PCT/US2014/010218, filed Jan. 4, 2014, which claims priority to U.S. Provisional Patent Application Ser. No. 61/749,086, filed Jan. 4, 2013, the disclosures of which are herein incorporated by reference in their entireties.

The present application claims priority to U.S. Provisional Patent Application Ser. No. 61/749,086, filed Jan. 4, 2013, the disclosure of which is herein incorporated by reference in its entirety.

TECHNICAL FIELD

Provided herein are systems, devices, and methods in the field of the biomedical sciences related to internal fixation of all types of orthopedic skeletal fractures as well as uses in the mechanical, aerospace, and architectural fields.

BACKGROUND

Current options for internal fixation of skeletal fractures and osteotomies include metallic devices consisting of stainless steel and titanium. These materials obscure the image of the fracture and osteotomy after their application due to their inherent property of radiopacity on X-ray evaluation. Carbon fiber in plating systems has been developed in the past, but have not exhibited the stability and durability of their metallic counterparts.

SUMMARY OF INVENTION

Carbon fiber reinforced with metal alloy mono and poly-filament wire corrects the current misfortunes of metallic plating systems by maintaining the rigidity of the plating system while decreasing the size (thickness) and weight of the current plating systems. The current metal alloy plate designs that would be replaced by the inventive devices are designed with a thickness ranging from 2.7 mm to 3.5 mm and allow for multiple device configurations and applications to aid in fracture or osteotomy fixation and stability. Arthrex ankle fracture plating system is an example of the various conformations and strengths for fracture plating systems. Examples of these plates include One/Third Tubular Locking Plates, 3.5 mm Reconstruction Plates, Locking Medial Hook Plates, Locking Lateral Hook Plates, and Complex Fibular Fracture Plates. All plates designed for use on the fibula have modifications that allow for easier use of either the Tight-Rope or syndesmotic screws (12). The orthopedic carbon fiber metal alloy wire composite of embodiments of the invention provide the strength and versatility of the current fracture plate designs while maintaining a thickness less than the existing models available (e.g., 25% less; 50% less; 75% less).

The minimal artifact/footprint observed on radiographic evaluation allows for direct visualization of the fracture site in all planes. The increase in structural integrity, rigidity and durability of the carbon fiber with monofilament metal alloy wire can also be implemented in many areas of mechanical and architectural fields where a lightweight high strength material is needed.

In some embodiments, the present invention provides a system or device comprising an orthopedic plate comprising a metal alloy mono and poly-filament wire inserted between layered carbon fiber in a non-continuous fashion. In some embodiments, the plate comprises at least one threaded shaft. In some embodiments, the device further comprises one or more screws sized to mate with the threaded shaft(s). In some embodiments, the threaded shaft and screw are configured to allow a plurality of angular orientations of the screw axis. In some embodiments, the screw has a threaded shaft and a head, wherein the threaded shaft and the screw head have a mating interface such that the screw engages the threaded shaft so as to cause a locked angular orientation of the screw axis in the threaded shaft. In some embodiments, the device comprises one or more screw portals permitting the use of non-locking and/or locking screws in any desired fashion. For example, in some embodiments, the screw portals comprise a metal or metal-allow ring placed circumferentially about the surface of the screw portal and parallel to the axis of the plate. In some embodiments, the inner diameter of the ring comprises threads for mating with the screw. In some embodiments, the ring is configured to permit angulation of a screw to be fixated to an osseous structure under the plate in thirty degrees from perpendicular to the plane of the plate. Rings may be selected with preset angles to guide the screw in the desired orientation relative to the surface of the place and/or bone. In some embodiments, the locking system comprising screw portals is directly part of the mono and poly-filament wire reinforcing system incorporated between layers of carbon fiber, while in other embodiments it is a separate, but attached, component.

The plate can take the form of any desired orthopedic plate. In some embodiments, the plate has a longitudinal axis, wherein the plate comprises a curve transverse to the longitudinal axis and wherein the plate has a constant radius along the longitudinal axis (e.g., along all or a portion of the length of the device; e.g., along a central trunk). In some embodiments, the plate is configured for internal fixation to a bone (e.g., human bone) selected from the group consisting of: tibia, fibula, femur, humerus, radius, ulna, skull, clavicle, scapula, pelvis, spine, ribs, mandible, calcaneus, talus, metatarsals, metacarpals, and orbitals. In some embodiments, the plate system comprises a central trunk which includes a neck; the central trunk and the neck having a complex contour ⅓ tubular design that forms a spoon shape toward a bone facing surface. Also provided herein are methods and uses employing such plates for the fixing of a bone of a subject (e.g., a human subject, a mammal, a companion animal, livestock, an equine, etc.).

Figure 15:
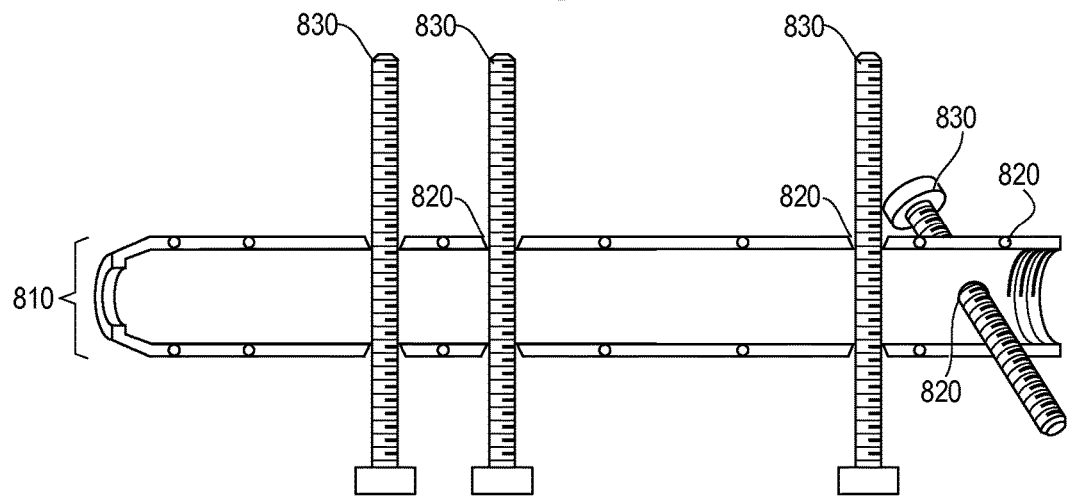
Figure 16:
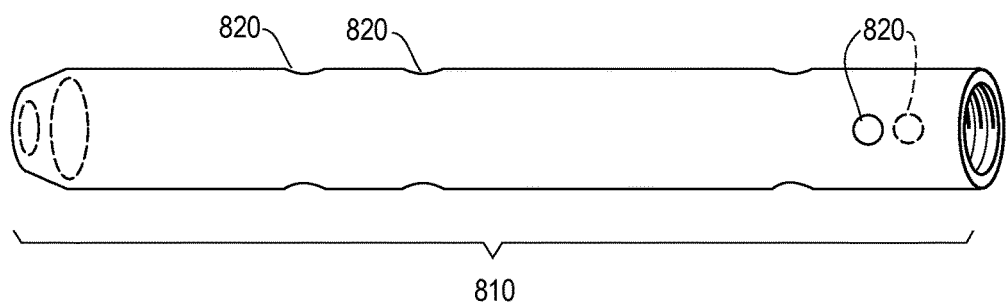
Figure 17:
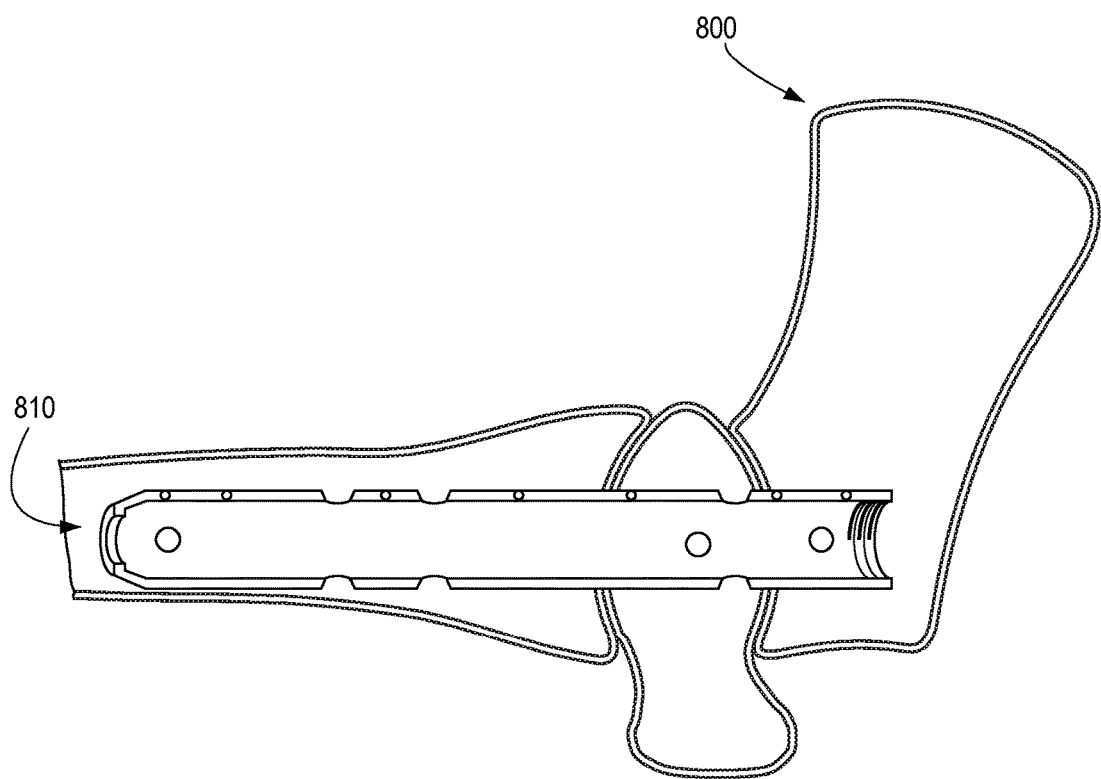

In some embodiments, see e.g., FIGS. 12-17, provided herein is a system comprising a metal alloy mono and poly-filament wire incorporated a carbon fiber sandwich panel forming a cylindrical tube or rod intramedullary nail 810 configured for the fixation of long bone fractures, osteotomies, or arthrodesis (e.g., inserted within a medullary canal cancellous bone in an anti-grade or retrograde orientation), said system further comprising screw portals 820. In some embodiments, the screw portals are configured such that locking screws or non-locking screws 830, when inserted into said screw portals, extend in a divergent manner from the nail and permit each end of screws to fixate cortical bone on each side of the intramedullary rod to be gripped by first and second locking screw or non-locking screws so as to stabilize said fractures, osteotomies, or arthrodesis. In some embodiments, the screw portals are positioned such that screws inserted therein pass through a non-articular portion of a cortical bone and fusion sites for joint arthrodesis, while gripping a cortical bone mass. In some embodiments, the intramedullary nail is designed for retrograde and anti-grade insertion into the long bones from distal to proximal or proximal to distal, and incorporates a component for attachment of a temporary jig to the distal or proximal portion of the intramedullary nail to facilitate drilling of pilot holes and subsequent insertion of locking or non-locking screws. In some embodiments, distal locking holes are positioned at a distal end of the nail, wherein said proximal and distal ends are comprised of a threaded axial hole. In some embodiments, the nail has one or more preformed proximal holes extending transversely through a proximal region of the nail to stabilize the intramedullary nail with respect to the shaft of the long bones. For example, FIG. 17 illustrates the intramedullary nail 810 inserted through the plantar aspect of the foot 800 and extended proximally toward the knee in a retrograde fashion to demonstrate the placement for tibio-talo-calcaneal fusion.

Systems and devices are provided herein that find use in any of a variety of medical, manufacturing, or industrials fields. In some embodiments, provided herein are methods for reinforcing carbon fiber sandwich paneling comprising: a) compressing mono and/or poly-filament metal alloy wires between layers of carbon fiber sheets, wherein a plurality of different wires are oriented in the sheets in different orientations, to form a carbon fiber sandwich; and b) curing the carbon fiber sandwich. In some embodiments, the wires comprise a plurality of different gauge wires. In some embodiments, the wires comprise a plurality of different non-linear orientations (e.g., coils, bends, loops, etc.). In some embodiments, a plurality of different wires are oriented in the sheets such that wires in a first layer are oriented in a first direction and wires in a second layer are oriented in a different direction (e.g., randomly, by defined angles, etc.). In some embodiments, the carbon fiber is prepared by vacuum resin infusion. In some embodiments, a heating element is applied or not applied during the curing process. Further provided herein are carbon fiber sandwich panels produced by any of the methods.

BRIEF DESCRIPTIONS OF THE DRAWINGS

Figure 1:
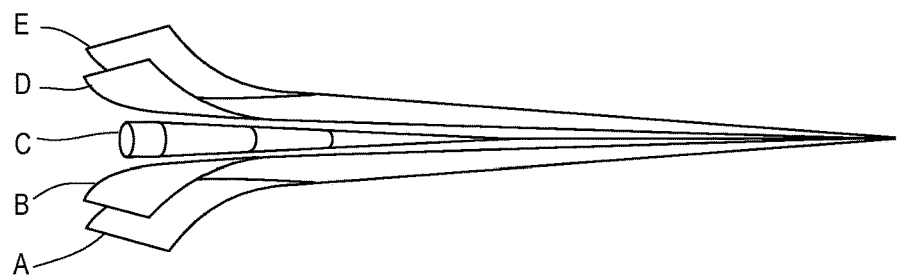

FIG. 1: An exemplary plate embodiment comprising layers of lamination under pressure sheets of Carbon fiber impregnated with epoxy resin and hardener and internal infrastructural framework of metal alloy mono and poly-filament wire of various gauges coated with fiberglass and epoxy resins.

Figure 2:
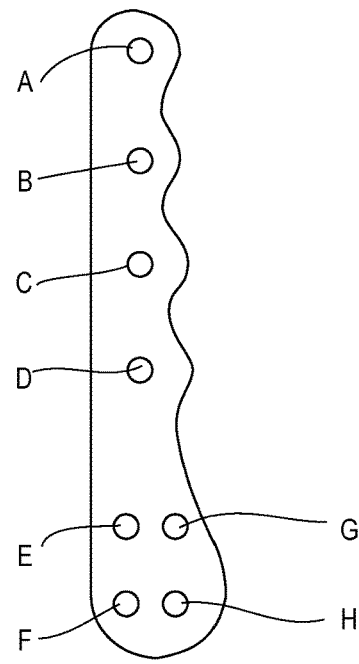

FIG. 2: Anterior view of an embodiment contoured fibular plating system of metal alloy mono and poly-filament wire reinforced carbon fiber for skeletal fracture fixation with screw portals accepting 3.5 mm to 5.5 mm cortical and cancellous locking or non-locking screws. Exemplary plate dimensions: Length 8 cm, width 2 cm proximal widest, width, 1.25 cm proximal thinnest, width 4 cm Distal, thickness 1 mm thinnest, thickness 1.25 mm thickest. Spoon shaped distally to accommodate for anatomic variance of the osseous structure. The posterior surface of the plate incorporates an alternating convex and concave of identical radius in which the concave radius is located adjacent to the screw portal on the proximal shaft. The screw placement on the shaft of the plate is located centrally 8 mm from the outer edge of the plate. The wire is located within the layers of carbon fiber in a non-continuous manner and 4 mm from and edge of the plate or screw portal. The plate comprises at least two layered sheets of carbon fiber with the wire of various metal types although titanium is most commonly used for infrastructural support. The metal alloy wire (titanium) gauge is 18 but may range from 12 to 32 gauges. Each screw portal (labeled A through H) is 1 cm from any other screw portal and contains both locking and non-locking attributes for 3.5 mm screw fixation.

Figure 3:
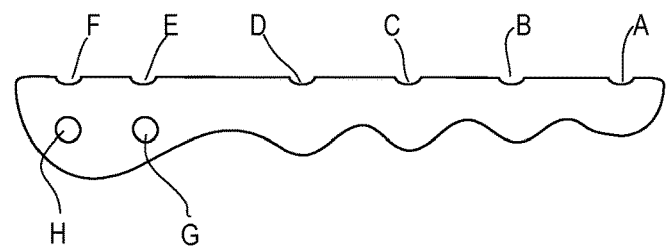

FIG. 3: Lateral profile view of an embodiment contoured fibular plating system of metal alloy mono and poly-filament wire reinforced carbon fiber for skeletal fracture fixation with screw portals accepting 3.5 mm to 5.5 mm cortical and cancellous locking or non-locking screws. A-H illustrate screw fixation portals strategically placed throughout the length of the carbon fiber with metal wire infrastructure plate. The screw placement on the shaft of the plate is located centrally 8 mm from the outer edge of the plate. Each screw portal is 1 cm from any other screw portal and contains both locking and non-locking attributes for 3.5 mm screw fixation. Each Screw portal is designed with screw guidance threads for locking and non-locking screw options. The threads within the screw portal have a constant pitch matching the pitch of the threads of the 3.5 mm screw to engage the plate and "lock".

Figure 4:

FIG. 4: Proximal to distal view of an embodiment contoured ⅓ tubular fibular plating system of metal alloy mono and poly-filament wire reinforced carbon fiber for skeletal fracture fixation with screw portals accepting 3.5 mm to 5.5 mm cortical and cancellous locking or non-locking screws.

Figure 5:
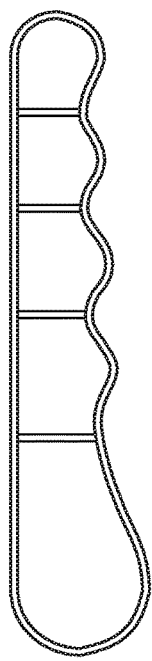

FIG. 5: An embodiment metal alloy mono and poly-filament wire reinforced carbon fiber of various gauges ladder type cross member infrastructure of wire with circumferential loop design. Screw fixation portals located adjacent to cross member ladder configuration.

Figure 6:
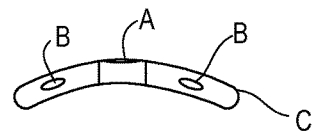

FIG. 6: Proximal to distal crossectional view of an embodiment of orthopedic plating system contoured ⅓ tubular design illustrating the locking and non-locking position for screw fixation with mono and poly-filament metal alloy wire reinforcement within the carbon fiber construct. Portion A illustrates a screw fixation portal with a threaded pitch oriented circumferentially around the portal. The threaded pitch is consistent with that of the 3.5 mm fixation screw to engage for locking and non-locking capability. Portion B illustrates an 18 gauge titanium wire insulated and incorporated within the carbon fiber sheets. The wire is located within the layers of carbon fiber in a non-continuous manner and 4 mm from and edge of the plate and screw portal. The plate comprises at least two layered sheets of carbon fiber. The wire is located within the layers of carbon fiber in a non-continuous manner and 4 mm from and edge of the plate or screw portal. Portion C illustrates the layers of carbon fiber forming the fracture fixation plate. The number of layers varies based on the amount of structural support desired and the amount of deforming forced placed on the plate to maintain anatomic alignment of the fracture following fixation.

Figure 7:
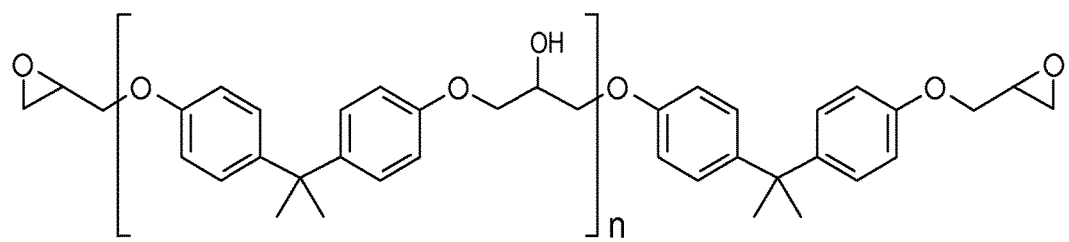

FIG. 7: Epoxy prepolymer resin chemical structure.

Figure 8:
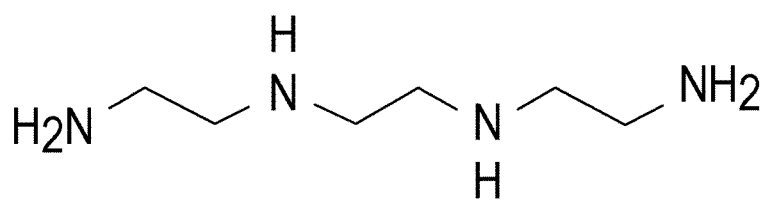

FIG. 8: Structure of TETA, a typical hardener. The amine (NH) groups react with the epoxide groups of the resin during polymerization.

Figure 9:
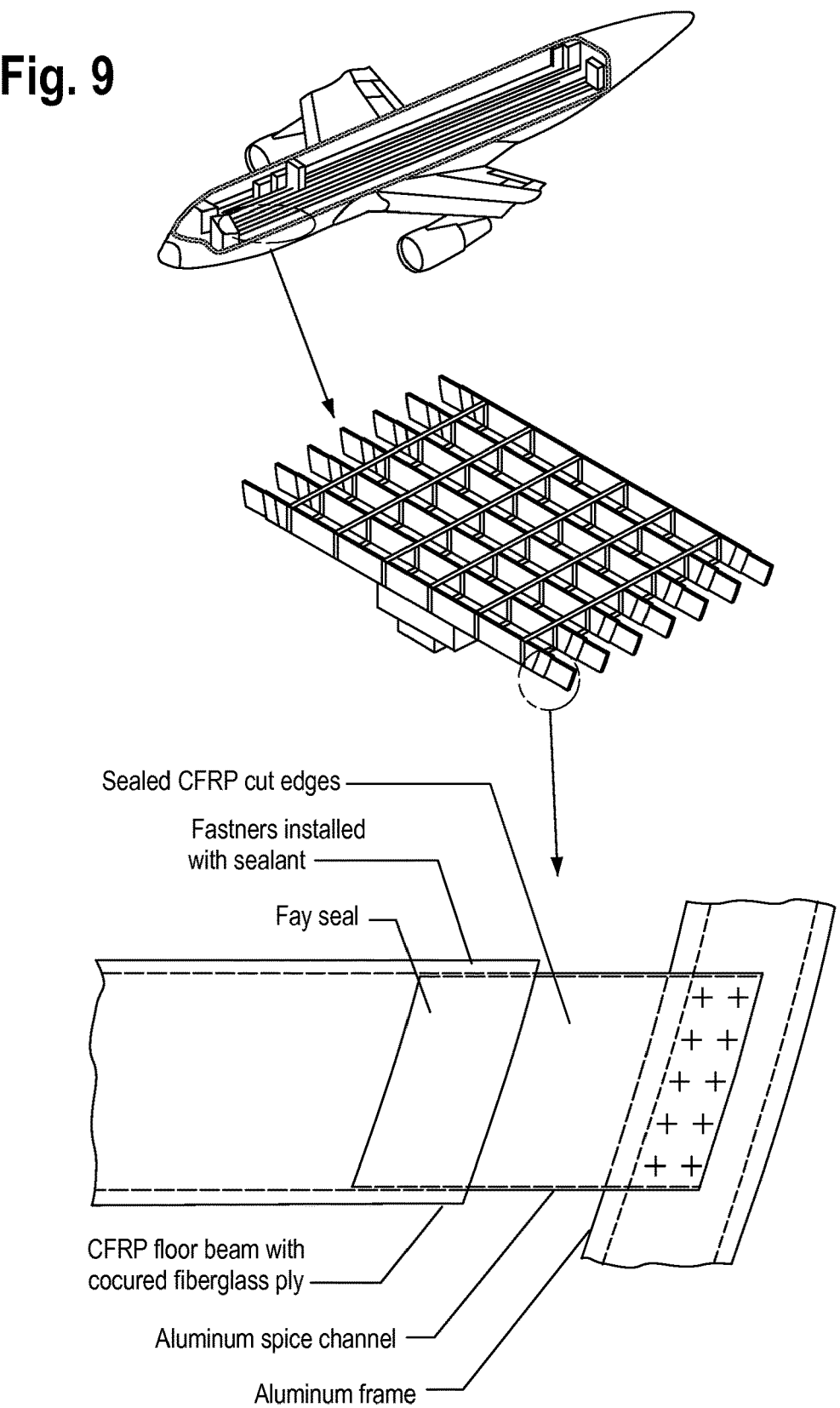

FIG. 9: The adaptation of composite materials in aerospace design in the Boeing 777 carbon fiber-reinforced plastic (CFRP) floor beam design and corrosion-protection methods. An aluminum splice channel is used to avoid attaching the floor beam directly to the primary structural frame.

Figure 10A:
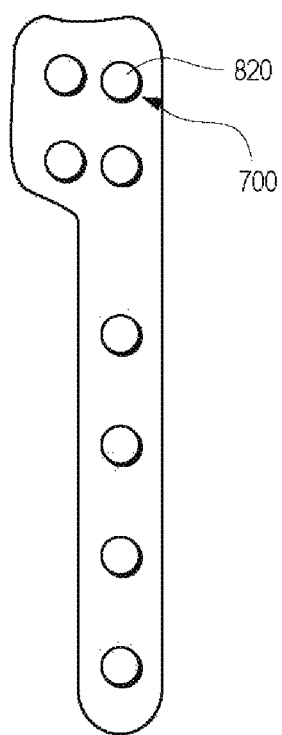
Figure 10B:
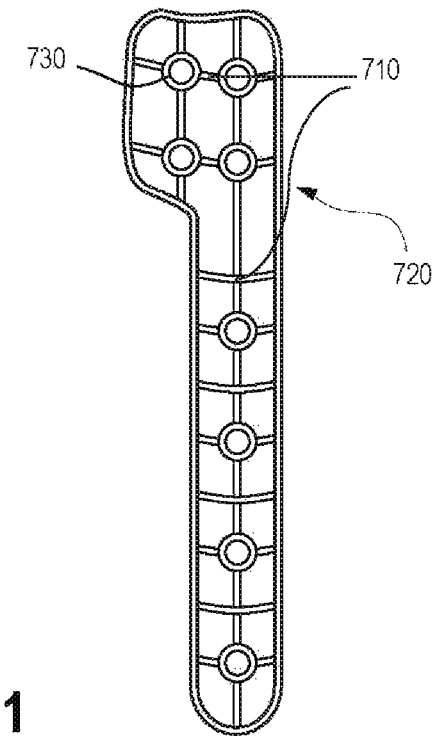

FIG. 10: Illustration of a mono or poly-filament wire infrastructure with locking washers at screw portal sites (FIG. 10A) coupled to the frame of the plate with additional wires extending from the locking portals to the existing wire frame prior to application of carbon fiber sheets (FIG. 10B).

Figure 11:
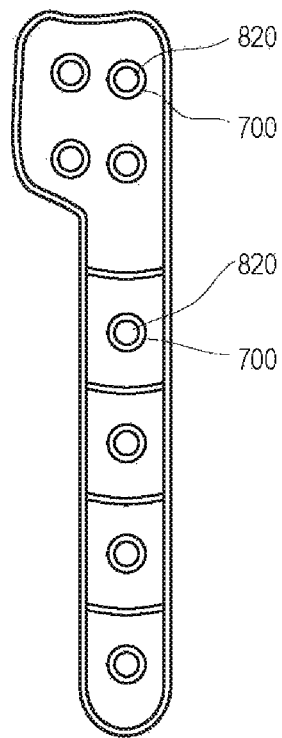

FIG. 11: Illustration of a mono or poly-filament wire infrastructure with locking washers at screw portal sites uncoupled to the frame of the plate, free standing from the existing frame.

Figure 12:
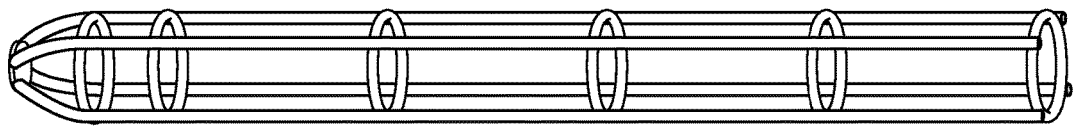

FIG. 12: Illustration depicting the mono or poly-filament wire infrastructure of an intramedullary nail, oriented in a circumferential lattice formation.

Figure 13:
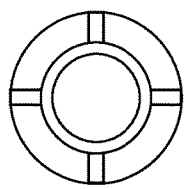

FIG. 13: Illustration depicting the mono or poly-filament wire infrastructure of the intramedullary nail from the apex of the nail, oriented in a circumferential lattice formation.

FIG. 14: Illustration of a carbon fiber intramedullary nail cross-section with mono or poly-filament wire infrastructure in a cylindrical formation extending the length of the intramedullary nail. Screw portals are noted in the transverse plane, perpendicular to the long axis of the intramedullary nail.

FIG. 15: Illustration of a carbon fiber intramedullary nail cross-section with mono or poly-filament wire infrastructure in a cylindrical formation extending the length of the intramedullary nail. Screw portals with screw placement are noted in the transverse plane, perpendicular to the long axis of the intramedullary nail.

FIG. 16: Illustration of the carbon fiber intramedullary nail with mono or poly-filament wire infrastructure in a cylindrical formation extending the length of the intramedullary nail. Screw portals are noted in the transverse plane, perpendicular to the long axis of the intramedullary nail.

FIG. 17: Illustration of the carbon fiber intramedullary nail cross-section with mono or poly-filament wire infrastructure in a cylindrical formation extending the length of the intramedullary nail. The intramedullary nail is inserted through the plantar aspect of the foot and extended proximally toward the knee in a retrograde fashion to demonstrate the placement for tibio-talo-calcaneal fusion.

DETAILED DESCRIPTION

Provided herein are systems, devices, and methods for fixing skeletal fractures, as well as uses in medical, biological, or industrial fields where fixing of object is desired. In some embodiments, a combination of metallic and carbon fiber are used in producing a fixing device that is suitably durable and strong, while at the same time sufficiently transparent to imaging technologies.

For example, in some embodiments, the devices contain the outstanding attributes of both metal alloys and carbon fiber, which results in a stable, durable, and radiolucent fracture fixation plating system. A metal wire infrastructure is employed that retains the rigidity of a metal alloy while not obscuring the field of vision for radiographic evaluation. Carbon fiber with mono and poly-filament metal alloy wire reduces the thickness as well as the overall weight of the plating structure. The reduction in overall weight of any implant is an advantage, which conserves the anatomical characteristics of the biological environment. It also minimizes the disruption of anatomic structures and the weight discrepancy between the surgical structure and surrounding structures. This aids in the recovery of the affected traumatic site of injury and patient satisfaction. The decline of both weight and the thickness of the plate prevents soft tissue irritation and the protrusion of the implant into the connective tissues. This in turn leads to a reduction of tissue strain during the incision closure and a faster healing process.

Previous studies have alluded to the corrosive interaction between metal alloys such as aluminum and carbon fiber. Boeing (U.S. Pat. No. 6,743,497) has solved this by coating the metal with fiberglass and epoxy resin to form a barrier surrounding the metal. This process eliminates the contact corrosion between the two materials. The fibers are good electrical conductors and they produce a large galvanic potential with the aluminum alloys used in airplane structure. The only practical and effective method of preventing corrosion is to keep moisture from simultaneously contacting aluminum structure and carbon fibers by finishing, sealing, and using durable isolating materials such as fiberglass, as well as providing drainage. FIG. 9 shows the adaptation of composite materials in aerospace design in the Boeing 777 carbon fiber-reinforced plastic (CFRP) floor beam design and corrosion-protection methods. An aluminum splice channel is used to avoid attaching the floor beam directly to the primary structural frame (5). The application of this method in aerospace design is excellent for increasing strength, reducing weight, and eliminating the corrosive properties of the materials.

The instant invention applies some of the principles used in aerospace technology by combining materials and exploiting the tremendous strength and lightweight attributes. To date there has been no suggestion of the use for these components in anatomic fracture fixation. The aerospace industry design and implementation of these components increases the structural integrity of the parts but the positioning of the components is not suitable for medical or anatomical uses.

Carbon fiber composite sandwich designs are currently in use within structural industries such as aerospace engineering and architectural reinforcement (17). The current construction properties of the panel use an aluminum honeycomb, foams, glass and other materials to form the composite. For example, the titanium core/carbon fiber sandwich panels have been tested and demonstrate that this type of structure can reduce/eliminate issues with moisture, fluid intrusion, issues with thermal expansion and corrosion while maintaining a significant weight and damage tolerance advantage over other structures. Titanium core material has proven its high working temperature (3500-6000 F), excellent shear properties, corrosion resistance, and weight savings (7).

The systems, devices, and methods of the present invention employ similar materials, but apply a different design. A composite sandwich combines the superior strength and stiffness properties of carbon fiber. By strategically combining these materials, one is able to create a final product with a much higher bending stiffness to weight ratio than with either material alone. For example, carbon fiber reinforced with metal allow wire may be employed to provide desired structural properties, e.g., bending, torsion, compression, and tension.

In some embodiments, a metal wire infrastructure and an outer coating of carbon fiber are combined. The reinforcement surface can be coated to prevent a chemical reaction with the matrix. For example, carbon fibers are commonly used in an aluminum matrix to synthesize composites showing low density and high strength. However, carbon reacts with aluminum to generate a brittle and water-soluble compound $Al_4C_3$ on the surface of the fiber. To prevent this reaction, the carbon fibers can also be coated with nickel or titanium boride (8). Galvanic corrosion can be prevented or reduced by proper material selection. That is, selection of combinations of metals are as proximal as possible in the galvanic series. These results apply a barrier coating to both the anodic and the cathodic metal. Examples include applying sacrificial coating (such as zinc to steel), applying or building nonmetallic films (e.g., anodizing aluminum alloys), and by providing cathodic protection (9). A previous study performed by Tayton 1983 resulted in the corrosion of stainless-steel screws used to fix carbon-fiber reinforced plastic (CFRP) plates to human fractures. This was compared with the corrosion on similar screws used to fix stainless-steel fracture plates. Corrosive changes were noted in both sets of screws with similar frequency and severity; however, the stainless-steel plates were 'in situ' almost twice as long as the CFRP ones, showing that the corrosive changes occurred more rapidly on screws in contact with CFRP. Nevertheless, over the implantation time necessary for bone healing, corrosion was very mild and there is no clinical contra-indication to the use of stainless-steel and CFRP together in this particular application (10). The instant invention provides a stable high strength design that prevents the deforming forces translated to the skeletal structure by using a metal alloy mono or poly-filament wire completely insulated from the carbon fiber, therefore obviating the galvanic corrosive nature of the dissimilar materials.

In 2001, Mohammadreza Tavakkolizadeh et al. preformed corrosion studies on carbon fiber and metal composites. The results of the research concluded; 1) The test results indicate the existence of the galvanic corrosion when there is a direct contact between a CFRP laminate and steel substrate. The Evans diagram shows that when steel and carbon fibers coated with a thin film of epoxy are coupled together, the corrosion rate of steel increases by a factor of 24 and 57, respectively, in a deicing salt solution and seawater, respectively, for the specimens tested. 2) The galvanic corrosion rate is directly related to the epoxy coating thickness. Applying a thin film of epoxy coating (0.1 mm) on saturated carbon fibers decreases the galvanic corrosion rate in seawater and deicing salt solution by seven- and fivefold, respectively. By using saturated carbon fibers and thicker epoxy coating (0.25 mm, typical of that used in wet layup), the galvanic corrosion rate in seawater and deicing salt solution decreased by twenty-one- and twenty-threefold, respectively. 3) The galvanic corrosion rate in the deicing salt solution was slightly higher than that in seawater (15% on average). The difference was more pronounced for carbon fibers with no epoxy coating (24%). 4) Sizing agents decrease the galvanic corrosion rate of the carbon fibers. In the case of exposed fibers, acetone was the most effective solvent (50% change) for removing the sizing agents. The CFRP specimens made of washed fibers showed lower corrosion rates (50%). 5) Considering the common cathodic reaction in CFRP laminates coupled with steel (the reduction of oxygen in solutions with pH>7) and the evolution of hydroxide ions on the carbon fibers, the use of a matrix with hydrolyzable links (ester bonds) should be avoided in applications exposed to nonacidic deicing salt solution and seawater. 6) Since the galvanic corrosion only initiates when there is direct contact between two dissimilar metals in the presence of an electrolyte, measures can be taken to eliminate one or both of these parameters and to eliminate this problem. The use of a nonconductive layer of fabric between carbon and steel, an isolating epoxy film on the steel surface, and a moisture barrier can be considered as a few preventive alternatives (13). These results illustrate the importance of preventing the galvanic corrosion, which degrades the composite fracture plating.

Carbon fiber is manufactured to different thicknesses that range from 0.006" to 0.013" and patterns, which enables variations in the ease of manipulation and strength. In weaving the weft or woof is the term for the yarn, which is drawn through the warp yarns to create cloth. Warp is the lengthwise or longitudinal thread in a roll, while weft is the transverse thread. A single thread of the weft, crossing the warp, is called a pick. Terms do vary, for instance in North America, the weft is sometimes referred to as the fill or the filling yarn (15, 16). The most commonly used weave pattern for carbon fiber is '2/2 Twill'. In this pattern the weft goes over two intersecting warps and then under two (hence 2/2) to create a woven fabric with a predominantly diagonal pattern to it. This weave pattern is looser than Plain Weave allowing the fabric to drape more easily which is especially useful when laminating into mold surfaces with compound curves and contours. The looser pattern of the weave means that it should be handled more carefully than plain weave and also that accidental distortion to the weave (relevant where cosmetic appearance is important) is more likely (14). Some other examples of carbon fiber include; Braids, which are continuous tubes (or sleeves) of woven carbon fabric. Elongating the braid (stretching it out) will reduce its diameter, allowing braids to be adjusted to be a perfect fit around mandrels or into tubes of varying diameter. Tapes are simply thin strips (usually supplied on a roll) of woven carbon fabric, most commonly plain weave. Tapes of woven carbon fibers are useful for providing localized reinforcement without the need to cut down large pieces of fabric. Satin weave, harness weave, fish weave etc. are all different weave patterns for carbon fabric although they are used much less widely than 2/2 Twill and Plain Weave. In advanced composites there are almost no situations where these weave patterns are used or are advantageous and so unless one has a very unusual requirement, one is unlikely to need or encounter these more obscure weaves. Rovings is the name given to the bunches of carbon fibers that are usually woven into fabrics. Unwoven rovings are sometimes used as localized reinforcement where they are often wound around a repair. Unidirectional carbon fiber is a reinforcement where all (or almost all) of the carbon fibers are aligned in the same direction. The only thing holding the fibers together will be occasional strands of either carbon or polyester running across the fibers at 90 degrees. Unidirectional material is used in applications where all of the forces on a part will be in one direction (such as the body of an archery bow). Alternate layers of unidirectional fibers can be positioned with different orientation to allow for added strength. Plain weave fabric is the second most widely used of the woven carbon fabrics. In this weave the weft goes over one warp and under the next, creating a grid-like pattern. Plain weave is a slightly tighter weave pattern that 2/2 twill and therefore easier to handle without distorting, however it is not as drape-able as 2/2 twill and therefore it is not the first choice for compound contours. The instant invention incorporates one or more of the stitch patterns in a layered fashion with a metal alloy wire infrastructure to provide the highest strength and durability to the final construct possible.

The process of manufacturing a carbon fiber composite requires a "glue" to maintain the final product. In some embodiments, the devices, systems, and methods of the invention employ an epoxy resin: epoxy is a copolymer; that is, it is formed from two different chemicals. These are referred to as the "resin" or "compound" and the "hardener" or "activator". The resin comprises monomers or short chain polymers with an epoxide group at either end. Most common epoxy resins are produced from a reaction between epichlorohydrin and bisphenol-A, though similar chemicals may replace the latter. The hardener comprises polyamine monomers, for example triethylenetetramine (TETA). When these compounds are mixed, the amine groups react with the epoxide groups to form a covalent bond. Each NH group can react with an epoxide group from distinct prepolymer molecules, so that the resulting polymer is heavily cross-linked, and is thus rigid and strong (4). The process of cross-linking is called "curing". Curing is hardening of the polymer by cross-linking of an existing polymer and can be controlled through temperature, choice of resin and hardener compounds, and the ratio of said compounds; the process can take minutes to hours. Some formulations benefit from heating during the cure period, whereas others simply require time and ambient temperatures (4).

Fracture fixation utilizing the currently available devices obscures the direct visualization of the fracture healing process. Plate thickness and overall weight has also been a concern of manufacturers. The goal of implant designs is to conserve the anatomic and physiologic nature of the pre-fracture state of the skeletal system. The current designs of metal alloy plating systems do not preserve the pre-fracture state by separating the soft tissues from the boney surface. The soft tissue surrounding the boney surface is often minimal and therefor delicate. An example of this is the lateral malleolus of the ankle, which is commonly fractured with ankle twisting injuries. The fixation often required is a metal alloy plate placed on the lateral aspect of the fibular malleolus. Placing the plate in this orientation leaves little soft tissue coverage on the bones of the ankle due to the overall thickness of the plate and is often a source of irritation and wound dehiscence. Carbon fiber plating with metal alloy mono and poly-filament wire of the instant invention corrects this common issue by reducing the thickness of the plate by 75% or more and translating less stress onto the surrounding tissues during the closure process.

Skeletal fracture and osteotomy fixation utilizing metallic plating systems has been employed in the field of orthopedics for centuries. AO foundation (Arbeitsgemeinschaft für Osteosynthesefragen (German for Association for the Study of Internal Fixation)) and Synthesis Corporation have standardized fixation manipulation and reduction using the principles of internal fixation including anatomic reduction, stable rigid fixation, maintenance of neurovascular structures and early return to activity. The current metallic plating systems achieve these principles while obscuring the radiographic visualization of fracture healing process and disrupting the soft tissue structures due to the thickness and overall weight.

The 5 phases of fracture healing are the following.
Fracture and inflammatory phase
Granulation tissue formation
Callus formation
Lamellar bone deposition
Remodeling The use of carbon fiber without reinforcement plating system allows motion at the fracture and osteotomy site contradicting the second principle of the AO foundation to restrict motion at the fracture site but allows observation of the site of trauma and surgical correction through radiographic evaluation. Although callus formation is a natural progression to the fracture healing process as noted in the 5 phases of fracture healing, too much callus formation is an indication of excessive motion, potentially leading to non-union of the fracture. The instant invention incorporating the metal alloy wire infrastructure intensifies the strength of the carbon fiber plate and diminishes the opportunity for motion at the fracture site following plate fixation. As previously stated the use of carbon fiber alone for skeletal fractures is inadequate due to the lack of rigidity (as reported by Ali et al. in 1990). While some embodiments for the instant invention find use for skeletal fracture fixation, the invention can be incorporated into multiple facets of architectural aerospace and mechanical genres to add supportive reinforcement to carbon fiber constructs.

The systems, devices, and methods of the invention can be applied to each of the plate design types for fracture fixation in all areas of the body. These plate types include,
1. Neutralization plate
2. Compression plate
3. Buttress plate
4. Bridging plate/wave plate
5. Antiglide plate
6. Tension-band plate
7. Spring plate Examples of fracture fixation plates include,
Neutralization Plate
  Protect lag screws from bending, shear, & rotation
  This plate design is commonly used in the internal fixation of lateral malleolus fracture
Compression Plate
  Applied to tension side of eccentrically loaded bone
  Can produce 600N compression (cf. 2000-4000N compression with lag screw)
  Plate should be over bent to produce compression on far side as well as near cortex
  Inner screws applied first
  Function of grooves on Limited Contact Dynamic Compression Plate (LCDCP)
    Improve blood circulation by minimizing plate-bone contact
    More even distribution of stiffness through the plate
    Allows small bone bridge beneath the plate
  This plate design is commonly used in the internal fixation of transverse or short oblique radial fracture
Buttress Plate
  Physically protects underlying thin cortex
  Often for metaphyseal fractures
  This plate design is commonly used in the internal fixation of tibial plateau & distal radius fractures
Bridging Plate
  Treatment of multifragmented fractures
  Bridge segment of comminution with indirect reduction & minimal disruption to blood supply
  Compression occasionally possible
  This plate design is commonly used in the internal fixation of comminuted ulnar fracture
Anti-Glide Plate
  Secured at apex of fragment of oblique fracture to physically block shortening or displacement
  This plate design is commonly used in the internal fixation of Weber B ankle fracture with posterior plate
Tension-Band Plate
  Same principle as Tension Band Wiring with application on tensile surface of eccentrically loaded bone & conversion of tension forces to compression forces
  This plate design is commonly used in the internal fixation of olecranon plate (11). The carbon fiber metal alloy wire composite plate contains the properties of each of these plates and has the ability to be conformed to all fracture types that require internal fixation. The carbon fiber metal alloy wire plate designs share all of the optimal attributes of each of the previously mentioned plate designs, while maintaining thinner, lighter, radiolucent, advantages without sacrificing strength to preserve anatomic reduction and stabile fixation of fractures throughout the body.

Previous carbon fiber fixation plating systems have failed to maintain a stable rigid construct when compared to stainless steel plates for similar types of fractures as noted by Ali et al. (3). The carbon fiber plating system without a metal alloy wire infrastructure allows motion at the fracture site contradicting the second principle of the AO foundation but allows observation of the site of trauma through radiographic evaluation. Minimizing motion at the fracture site provides an optimal environment for fracture healing as noted by the AO foundation. Embodiments of the instant invention with a metal alloy wire infrastructure provides the stability required for rigid internal fixation of skeletal fractures and has applications in surgical and fracture fixation of all boney structures in the body including the tibia, fibula, femur, humerus, radius, ulna, skull, clavicle, scapula, pelvis, spine, ribs, mandible, calcaneus, talus, metatarsals, metacarpals, orbitals, etc. where a surgeon of ordinary training can apply the principles of open reduction with internal fixation of skeletal fractures and osteotomies.

Combining the carbon fiber and metal alloy wire reinforcement increases the internal rigidity of the plating system while retaining the radiolucent properties of the carbon fiber. The metal alloy mono and poly-filament wire is radiopaque but has a minimal signature and therefore allows radiographic visualization of the fracture site. Ali et al. noted minimal inflammatory response or signs of rejection produced in biologic environments when exposed to the epoxy resin (3). Combining the carbon fiber and metal alloy wire reinforcement with an epoxy resin can be adapted safely to the physiologic environment with minimal inflammatory response.

The combination of carbon fiber and metal allows for a composite material with increased strength added to the surgical construct. The embodiments of the instant invention can further take on many forms including tubular structures to create a frame apparatus with function in building support, automobiles, bicycles etc. The orientation of the metal alloy can be manipulated into many different designs such as lattice helical parallel and random orientations to provide the construct with the greatest strength, durability and visualization during radiographic examination while maintaining the low-profile and lightweight properties of the carbon fiber and metal allow composite structures as described.

Metal alloy reinforced carbon fiber is configured to increase strength and durability of the surgical construct when applied to open reduction with internal fixation of skeletal fractures and surgical osteotomies. Current applications of metal filaments matrices are embedded and completely continuous with carbon fiber and have not been applied to the surgical arena. The metal alloys most commonly used are aluminum cobalt titanium and magnesium. While these methods of combining the material in a cohesive material does increase strength and durability in the instant invention, the radio opacity common to the prior art is not maintained.

The method of structurally combining a metal alloy with carbon fiber in a non-continuous manner is ideal for fracture fixation due to the low profile design, which maintains a lightweight, rigid, and radiolucent construct. This method calls for a structural backbone of a metal alloy wire of various gauges custom fitted to the shape of the plate designed for maximum stability for specific skeletal fractures throughout the human body. The metal alloy wire is insulated from the carbon fiber to prevent galvanic corrosion. The method of insulating the wire is preformed with a coating of fiberglass, nickel or titanium boride. Coating the cathode (metal alloy) with the materials mentioned decreases the contact of the cathode and anode (carbon fiber) and therefore prevents the electrochemical reaction resulting in galvanic corrosion. The metal alloy wire can be formed into many different patterns as including a spoon shape contoured ⅓ tubular design as previously shown in the preferred embodiment FIG. 2. A carbon fiber negative mold of the desire plate is fashioned using standard molding techniques and coated with a non-adhesive wax. The positive plate mold of the plate desired is created by one sheet of carbon fiber and epoxy resin as well as hardener. The carbon fiber is press fitted manually into all recesses of the negative carbon fiber mold after a releasing wax has been applied to the negative mold for removal following all applications of the carbon fiber and metal alloy wire coated with insulating material, epoxy, and hardener. An additional layer of carbon fiber is applied to the first in the same fashion. A metal alloy wire of various gauges coated with a layer of material (e.g., fiberglass, resin, etc.) to decrease the interface between the poly mono-filament wire and in turn to resist the corrosive nature of the materials is then placed over the first two layers of carbon fiber. Thin hollow metallic disks made of the same material as the screw, resembling a washer (see e.g., FIG. 10A showing washers 700 positioned over screw portals 820) are placed at the screw portals as an option to allow for locking the screw to the plate either by fashioning threads into the washers with pressure and cutting from the screw or having threads in the screw prior to placement of the washers in the plate at the screw portal. The non-locking screw portals do not incorporate additional materials at the screw portal sites and locking screw portals are formed by metal, metal-alloy rings are placed circumferentially about the screw portals parallel to the long axis of the plate, threads are fashioned within the internal portions of the metal, metal-alloy rings contact point of the screw and the plate. As shown in FIG. 10B, the locking screw fixation portals may be adjoined to the mono and or poly-filament reinforcing wire or freestanding from contact with the mono or poly-filament reinforcing wire. The adjoined locking screw portals contact the mono or poly filament reinforcing wires by additional mono or poly-filament wires between the same layer of the carbon fiber as the surrounding reinforcing mono or ploy-filament wire (see e.g., FIG. 10B showing intermediate wires 710 connected to the rings 730 and interconnected to the wire 720 of the mono or poly-filament). FIG. 11 shows an alternative design with washers 700 at screw portals 820, but where locking washers at screw portal sites are uncoupled to the frame of the plate, free standing from the existing frame.

Two more applications of carbon fiber are then placed over the metal alloy wire in the same fashion as the first two carbon fiber sheets in order to completely encapsulate the wire. The mono and or poly-filament metal alloy wire of various gauges is manipulated into various orientations and compressed between layers of carbon fiber sheets orienting the carbon fiber threads in random or various degrees between the layers. A sheet of non-stick fabric followed by infusion fabric is applied to the carbon fiber prior to the vacuum bag and sealing tape. The entire mold is then vacuum-sealed to 30 cfm (cubic feet per minute) and allowed to cure until hard. The epoxy resin and hardener are infiltrated throughout the mold in a 2:1 ratio. The positive carbon fiber with incorporated metal alloy wire is now released from the negative mold following the curing stage completion. Screw fixation portals are fashioned into the carbon fiber mold for screw fixation points. These include both locking and non-locking configuration, which are added following completion of the positive mold. The screw portals remain a 4 mm distance from the metal alloy wire contained within the carbon fiber. The product is sterilized by any desired standard means of sterilization technique to prevent biological contamination prior to implantation of the device. The standard means of sterilization include dry heat sterilization, moist heat sterilization, chemical sterilization, and ionizing radiation sterilization. The gauges of mono and poly-filament wire vary as well as do the number of layers of carbon fiber to provide the thinnest most stable construct.

The plate design entails two or more portals for enabling fixation and is 0.1 cm in thickness. The metal alloy wire may comprise one or more of the following aluminum, titanium, stainless steel, nickel, cadmium, cobalt, magnesium, tungsten, gold, silver, platinum, or copper. The reinforcement of the plate can be achieved with high strength polymers using the same method. The metal alloy filament gauges vary as to mono and poly-filament and the dimensions of wire incorporated into the design range from 12 to 32 gauge.

The fixation portals located within the central portion of the plating system are adjacent to the metal alloy filament and accommodate 3.5 mm and 5.5 mm cortical, cancellous, locking and non-locking screw fixation. At least one screw has a threaded shaft and a head and wherein a screw hole and the screw head have a mating interface such that the screw can engage the plate screw hole so as to allow a plurality of angular orientations of the screw axis.

The size, shape, and configuration of the metal alloy wire can be selected and configured for the particular type of plate used. For buttress, neutralization, bridging, compression, tension band, and anti-glide plates, larger gauge wire and additional sheets of carbon fiber may be used due to the increased deforming forces placed on the fixation implements. In some embodiments, a titanium wire element is 12-32 gauge and remains 4 mm from the edge of the plate to avoid delamination. The wire is configured into a grid, helical, hexagonal, parallel, circular, or braided pattern. The grid pattern allows the wire to be placed in 90 degrees increments from its subsequent connection to the adjacent titanium wire. Additional grid patterns include 2-way, 3-way and 4-way orientations. The hexagonal configuration connects the wires in a 120 degrees structure in which no wire protrudes through the edges of the plate and screw portals. The parallel formations of the wires are fixed within the plate 4 mm from the adjacent wire in the same orientation throughout the length of the plate. The circular configurations of the wires are placed circumferentially around the screw portals and connected to the adjacent wire placed circumferentially around the next screw portal. Each of the wire configurations maintains the original plate design. For exemplary spring plates, smaller gauge wires (e.g., 18-32 gauge wires) are added to the infrastructure of the plate in a crossing figure eight pattern in a non-continuous manner. For exemplary tubular intramedullary nail devices, the wire infrastructure is added in a double helical or crossing helical pattern where the helix angle is oriented to gain maximum structural stability while allowing screw fixation points through the intramedullary nail (see e.g., FIGS. 12 and 13). Additional wire orientations for tubular implementations include parallel and hyperboloid configurations. The metal alloy wire is placed the through the length of the intramedullary nail.

While the current embodiment is designed for plate fixation following fracture or osteotomies within the surgical theater, additional configurations can be preformed accomplishing the same result. One of the additional embodiments is intramedullary rod in which a cylindrical orientation is arranged. The cylindrical carbon fiber rod contains the mono-poly filament metal/metal-alloy wire. The wire infrastructure further reinforces the mechanical strength of the carbon fiber construct.

The intramedullary nail can be implanted within the cancellous tissue of long bones either in an anti-grade or retrograde fashion depending on the location of the fracture, osteotomy or arthrodesis site. Retrograde intramedullary nail insertion is defined as the insertion of the rod from a beginning point of the bone distal from the center of the body and extending proximally toward the center of the body. Anti-grade intramedullary nail insertion is defined as the insertion of the rod at a proximal point and extending distally away from the center of the body.

Example 1

Fracture Fixation Plate Example, Fibula—is pre-contoured ⅓ tubular plate with a concentric superior surface to allow for maximal strength with minimal prominence to the adjacent tissues. The ⅓ tubular design is comprised of a curve transverse to the longitudinal axis has a constant radius along the longitudinal axis for at least a portion of the central trunk. The anterior surface remains without curvature and the posterior surface allows for curvature for limited contact and interface with the surrounding surfaces. The distal aspect of the plate is the anatomically contoured in a spoon shape to the distal portion of the osseous surface to allow for a larger surface area and acceptance of multiple fixation portals.

This combination of metal alloy wire to reinforce carbon fiber increases the resistance to bending, torsion, and tension deforming forces while maintaining the radiolucent properties of carbon fiber. This enables the physician to directly visualize the progression of fracture and osteotomy healing following open reduction with internal fixation of skeletal fractures and surgical osteotomies while maintaining the increased structural rigidity and durability of metal alloy fixation. This design therefore keeps the structural advantages of a metal alloy plate, while overcoming its disadvantages of being radiopaque.

The described invention has applications in multiple fields of structural categories of architectural, mechanical, and aerospace fields. While the preferred embodiment is used in surgical fixation of skeletal fractures and osteotomies the increased rigidity and durability of the design allows for functional implementation into areas of engineering where lightweight, high strength materials are required.

REFERENCES

1) Frost H M. The biology of fracture healing. An overview for clinicians. Part I. *Clin Orthop Relat Res*. November 1989; 248:283-93.
2) Szczêsny G, Interewicz B, Swoboda-Kopec E, Olszewski W L, Górecki A, Wasilewski P. Bacteriology of callus of closed fractures of tibia and femur. *J Trauma*. October 2008; 65(4):837-42.
3) M. S. Ali; T. A. French; G. W. Hastings; T. Rae; N. Rushton; E. R. S. Ross; C. H. Wynn-Jones. Carbon Fibre Composite Bone Plate: Development, evaluation and Early Clinical Experience. JBJS. (Br). 1990; 72-B:586-91.
4) http://en.wikipedia.org/wiki/Epoxy
5) http://www.boeing.com/commercial/aeromagazine/aero_07/corrosn.html#fig14
6) http://element6composites.com/technical-cf.asp
7) http://www.benecorinc.com/titanium.php
8) http://www.princeton.edu/~achaney/tmve/wiki100k/docs/Metal matrix composite.

9) Elements of Metallury and Engineering Alloys by Flake Campbell Page 328, 2008.
10) Tayton K. Corrosive effect of carbon-fibre reinforced plastic on stainless-steel screws during implantation into man. J Med Eng Technol. 1983 January-February; 7(1): 24-6.
11) http://www.orthofracs.com/adult/trauma/principles/fracture-classification/internal-fixation.html
12) http://www.arthrex.com/foot-ankle/ankle-fracture-plates
13) Mohammadreza Tavakkolizadeh, 1 Student Member, ASCE, and Hamid Saadatmanesh, 2 Member, ASCE GALVANIC CORROSION OF CARBON AND STEEL IN AGGRESSIVE ENVIRONMENTS JOURNAL OF COMPOSITES FOR CONSTRUCTION/AUGUST 2001 Vol. 5, No. 3, 200-210.
14) http://www.easycomposites.co.uk/Learning/Carbon-Fibre-Cloth-Explained.aspx
15) Barber, E. J. W. (1991). Prehistoric Textiles. Princeton University Press.
16) Burnham, Dorothy K. (1980). Warp and Weft: A Textile Terminology. Royal Ontario Museum.
17) J. Xiong, L. Ma, S. Pan, L. Wu, J. Papadopoulos, A. Vaziri. Shear and bending performance of carbon fiber composite sandwich panels with pyramidal truss cores. Acta Materialia 60 (2012) 1455-1466

I claim:

1. A device for use in skeletal fixation, comprising: an orthopedic plate comprising at least one metal alloy mono-filament and/or poly-filament wire infrastructure between at least two sheets consisting of carbon fiber, resin, and hardener, wherein said wire infrastructure is positioned to provide reinforcement and increase internal rigidity of said plate while retaining radiolucent regions of said plate.

2. The device of claim 1, wherein said plate comprises at least one threaded screw hole.

3. The device of claim 2, further comprising a screw sized to mate with said threaded screw hole.

4. The device of claim 3, wherein said threaded screw hole and screw are configured to allow a plurality of angular orientations of screw axis.

5. The device of claim 3, wherein said screw has a threaded shaft and a head and wherein said screw has a mating interface such that said screw engages said threaded screw hole to cause a locked angular orientation of the screw axis in said threaded screw hole.

6. The device of claim 1, comprising a screw portal comprising a metal or metal-alloy ring placed circumferentially about the surface of said screw portal parallel to the axis of said plate.

7. The device of claim 6, wherein said ring comprises threads configured for mating with a screw.

8. The device of claim 7, wherein said ring is configured to permit angulation of a screw to be fixated to an osseous structure under said plate in thirty degrees from perpendicular to the plane of said plate.

9. The device of claim 1, wherein said plate has a longitudinal axis and wherein said plate comprises a curve transverse to the longitudinal axis and wherein said plate has a constant radius along the longitudinal axis.

10. The device of claim 1, wherein the plate is configured for internal fixation to a human bone selected from the group consisting of: tibia, fibula, femur, humerus, radius, ulna, skull, clavicle, scapula, pelvis, spine, ribs, mandible, calcaneus, talus, metatarsals, metacarpals, and orbitals.

11. The device of claim 1, wherein said plate comprises a central trunk which includes a neck, said central trunk and said neck having a complex contour ⅓ tubular design that forms a spoon shape toward a bone facing surface.

12. A method of fixing a bone, comprising: affixing said device of claim 1 to a bone of a subject.

13. The device of claim 1, wherein said orthopedic plate is selected from the group consisting of a neutralization plate, a compression plate, a buttress plate, a bridging plate, a wave plate, an antiglide plate, a tension-band plate, and a spring plate.

14. The device of claim 1, wherein said metal alloy comprises one or more of aluminum, titanium, stainless steel, nickel, cadmium, cobalt, magnesium, tungsten, gold, silver, platinum or copper.

15. The device of claim 1, wherein said at least one mono-filament or poly-filament wire is coated with a coating selected from the group consisting of fiberglass, nickel or titanium boride.

16. The device of claim 1, wherein said carbon fiber sheets are woven carbon fiber fabrics.

17. The device of claim 1, wherein said wire infrastructure is positioned such that said plate has a higher bending stiffness to weight ratio than said wire infrastructure or said carbon fiber sheets alone.

18. The device of claim 1, wherein said wire is titanium wire.

19. The device of claim 1, wherein said wire infrastructure is located in a non-continuous manner at a distance from an edge of said plate.

* * * * *